United States Patent [19]
Bock

[11] 3,992,109
[45] Nov. 16, 1976

[54] CYCLIC COLORIMETRY METHOD AND APPARATUS

[75] Inventor: Ditmar H. Bock, Boston, N.Y.

[73] Assignee: Calspan Corporation, Buffalo, N.Y.

[22] Filed: Sept. 15, 1975

[21] Appl. No.: 613,647

Related U.S. Application Data

[63] Continuation of Ser. No. 341,438, March 15, 1973, abandoned.

[52] U.S. Cl. .............................. 356/181; 23/230 R; 23/253 R; 250/565; 250/573; 356/205
[51] Int. Cl.² .......................................... G01J 3/50
[58] Field of Search .......... 23/230 R, 232 R, 253 R, 23/254 R; 250/564, 565, 573, 574, 576; 356/180, 181, 184–186, 195, 201, 205

[56] References Cited
UNITED STATES PATENTS

| | | | |
|---|---|---|---|
| 1,977,359 | 10/1934 | Styer | 23/232 R X |
| 2,389,046 | 11/1945 | Hare | 23/232 |
| 3,089,382 | 5/1963 | Hecht et al. | 356/181 |
| 3,549,262 | 12/1970 | Hozumi | 250/576 |
| 3,643,102 | 2/1972 | Harper et al. | 356/180 |
| 3,708,265 | 1/1973 | Lyshkow | 356/181 |
| 3,729,263 | 4/1973 | Engholdt | 356/184 |
| 3,748,044 | 7/1973 | Liston | 356/180 |

Primary Examiner—John K. Corbin
Assistant Examiner—F. L. Evans
Attorney, Agent, or Firm—Allen J. Jaffe

[57] ABSTRACT

A process of and apparatus for colorimetry, whereby an indicator is added cyclically to a fluid stream to indicate the presence or absence of a condition in the stream. The presence of the condition may be indicated by the formation of a precipitate, a change of color, etc. A light source and photocell are located downstream of the point of addition of the indicator and by the difference in an optical characteristic such as the transmissivity or scattering of the fluid, at one or more wavelengths, due to the introduction of the indicator, a measure is obtained of the degree to which the tested-for condition is present in the fluid.

2 Claims, 3 Drawing Figures

U.S. Patent
Nov. 16, 1976
3,992,109
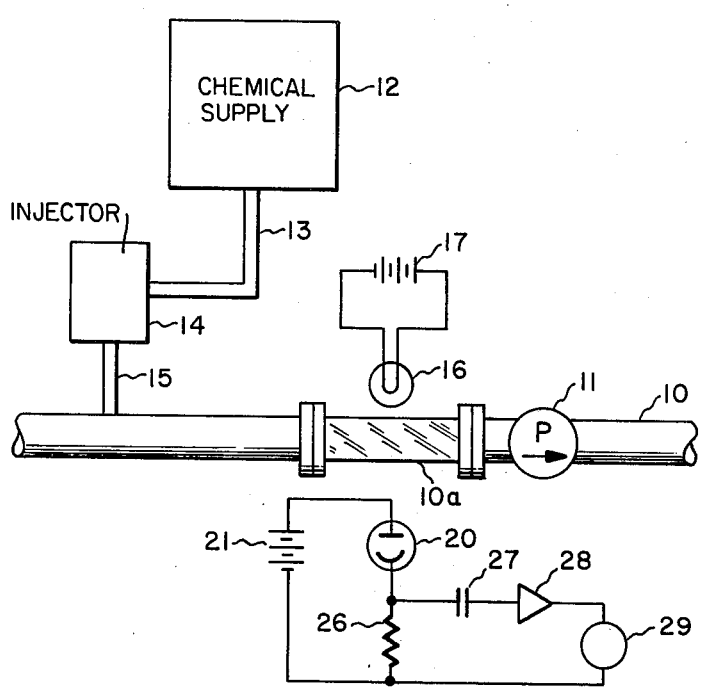
FIG 1.
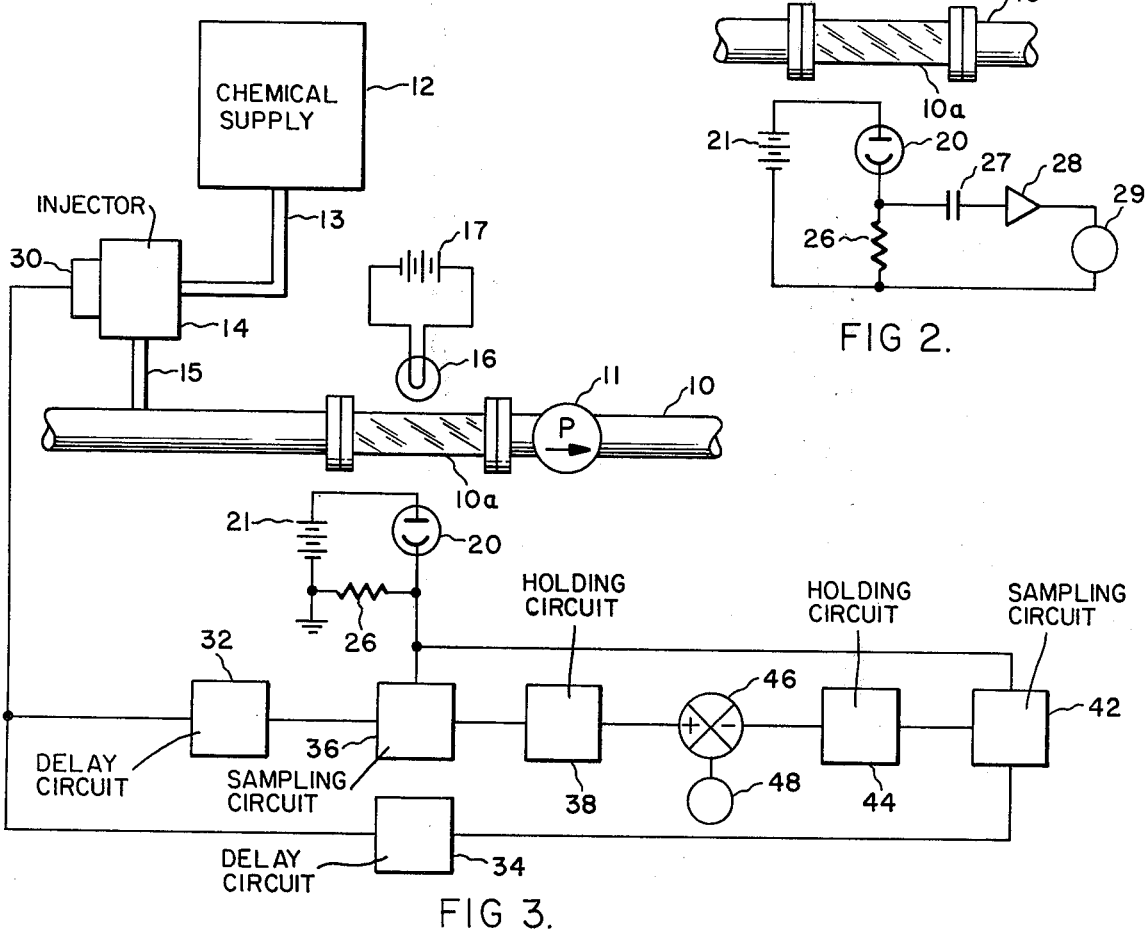
FIG 2.
FIG 3.

CYCLIC COLORIMETRY METHOD AND APPARATUS

This is a continuation of application Ser. No. 341,438, filed Mar. 15, 1973, now abandoned.

The present invention relates to the broad field of colorimetry and, more specifically to the use of colorimetry for detecting hazardous chemicals in water or air.

It is an object of this invention to detect the presence of a chemical in a liquid or gas by the use of colorimetry.

It is an additional object of this invention to provide a reliable colorimetric device which can be emplaced where the fluid to be tested varies slowly in color, turbidity or transmissivity.

It is a further object of this invention to provide a system whereby a minimum of indicator is added to the fluid to provide lower operating costs and to minimize the polluting effects of the indicator. These objects, and others as will become apparent hereinafter, are accomplished by the present invention.

Hazardous chemical spills should be detected quickly, both to limit damage to biotae and to facilitate treatment which is most effective when the spill is still concentrated. Although many spills cannot be anticipated, in certain probable locations such as industrial rivers, detector arrays could be effective at a reasonable cost. The detectors should be suitable for unattended, long-term use where a spill may reasonably be expected.

Among applicable methods for detecting pollutants in water, electrical conductivity is effective in detecting the presence of ionic solutes; pH and certain other specific ion probes are useful for indicating the presence of acids, bases and metallic pollutants. A variety of other compounds, especially heavy metal pollutants such as manganese, iron, cobalt, nickel, copper, zinc, silver, cadmium, antimony, mercury and lead, are detectable with a cyclic colorimeter.

In prior art devices the use of colorimetry is unsatisfactory where the fluid to be tested varies slowly in color, turbidity or transmissivity so as to mask the condition to be tested for due to the similar optical characteristics of the contaminant and the final indication. For example, silt which has an ochre appearance would mask or give an erroneous indication of the presence of manganese in a sulfide test because manganese sulfide is also ochre in appearance.

Heretofore this problem has been overcome by a careful sample preparation process such as centrifuging, filtering, etc. in order to remove the interfering contaminant such as silt. These processes are costly, time consuming and may even be inaccurate due to the removal of the constituent being tested for. Moreover, such existing processes are impractical for in situ measurements which are currently essential in pollution control efforts directed to industrial effluents.

Basically the present invention provides a method of and apparatus for cyclic colorimetry suitable for use in the presence of interfering contaminants which comprises introducing an indicator into a fluid then measuring and comparing the transmissivity or scattering of the fluid with and without the indicator whereby the presence of a condition of the fluid may be determined by the difference in transmissivity or scattering.

BRIEF DESCRIPTION OF THE DRAWINGS

For a fuller understanding of the present invention reference should now be had to the following detailed description thereof taken in conjunction with the accompanying drawings wherein:

FIG. 1 is a schematic diagram showing the use of the invention for detecting the presence of a chemical in the fluid;

FIG. 2 is a partial schematic diagram showing the use of the invention for determining a condition of the fluid; and FIG. 3 is a schematic diagram showing a modified form of the invention.

DESCRIPTION OF THE PREFERRED EMBODIMENTS

In FIG. 1, 10 represents a line carrying fluid to be tested and may, in practice, be the main line, a branch line, a sampling bypass line or even a freely falling stream. Line 10 may be made of any suitable material but a section 10a, thereof, must be made of a transparent material such as glass or plastic where line 10 is in fact a pipe. If necessary, a pump 11 is located in line 10 to provide a sufficient and/or regulated flow of fluid in line 10. A regulated supply of chemical is supplied to line 10 via line 15 by injector mechanism 14 which may take the form of a dosing pump, syringe, needle valves or other conventional structure. The chemical is furnished to the injector mechanism 14 via line 13 from a chemical reservoir or storage container 12. A light source 16 powered by a power source 17 transmits light through section 10a of line 10. A photocell 20 is located opposite light source 16 with section 10a of line 10 therebetween. A power source 21 and resistor 26 are located in series with photocell 20 and one of the terminals of resistor 26 is connected by means of an AC coupling capacitor 27 to the amplifier 28 and AC meter 29.

In the cyclic colorimetry system of FIG. 2, the numerals used in FIG. 1 have been used to designate similar structure. The system of FIG. 2 differs from that of FIG. 1 in the use of a filter 18 located intermediate light source 16 and section 10a of line 10.

In the cyclic colorimetry system of FIG. 3, the numerals used in FIG. 1 have been used to designate similar structure. The system of FIG. 3 differs from that in FIG. 1 in the use of a synchronous demodulating system to discriminate against random fluctuations in transmissivity as might occur if a fish, debris, etc. should pass through line section 10a. An injection sensor 30 senses the injection of the chemical into line 10 by the injector mechanism 14 and furnishes a signal to delay circuits 32 and 34. A sampling circuit 36 is connected to delay circuit 32, photocell 20 and holding circuit 38. A sampling circuit 42 is connected to delay circuit 34, photocell 20 and holding circuit 44. A subtracting circuit 46 is connected to holding circuits 38 and 44 and to meter 48.

The operation of the process of FIG. 1 is as follows: fluid is pumped through line 10 by pump 11 and passes between light source 16 and photocell 20. Fluctuations in the transmissivity or scattering of the fluid passing through section 10a of line 10 are indicated on meter 29 which is connected to photocell 20 by means of AC coupling capacitor 27. A source of chemicals 12 and an injector mechanism 14 are located upstream of section 10a to inject a slug of indicator into line 10. If the tested-for condition is present in line 10, the addition of the indicator will change the transmissivity or scattering of the fluid and the difference will be indicated on meter 29. This process is particularly applicable for the testing of a fluid for the presence of heavy metals especially those forming a sulfide precipitate.

EXAMPLE I

To detect the presence of iron sulfate (clear) in a dilute water solution, concentrated sodium sulfide solution (clear) is added to the dilute water solution to be tested. If iron sulfate is present, a black precipitate, iron sulfide will result which can be detected by the method and apparatus of this invention.

The operation of the process of FIG. 2 is as follows: fluid is pumped through line 10 by pump 11 and passes between light source 16 and photocell 20. Fluctuations in the transmissivity or scattering of the fluid passing through section 10a of line 10 are indicated on meter 29 which is connected to photocell 20 by AC coupling capacitor 27. A filter 18 of an appropriate color is located intermediate light source 16 and line section 10a. A source of chemicals 12 and an injector mechanism 14 are located upstream of section 10a to inject a slug of indicator into line 10. If the tested for condition is present in line 10, the addition of indicator will change the color of the fluid and hence its transmissivity or scattering and the difference will be indicated on meter 29. This process is particularly applicable for the testing for pH where there is a change of color by the indicator.

EXAMPLE II

To detect the presence of any acid, bromothymol blue containing a trace of base (blue) turns red in the presence of any acid. The use of a blue filter in the instant invention would permit the transmittance of less light through line 10a when the fluid has been turned red by the introduction of bromothymol blue in the presence of an acid in the fluid in line 10. This change in the transmittance of the light can be detected by photocell 20 and indicated on meter 29.

The operation of the process of FIG. 3 is as follows: fluid is pumped through line 10 by pump 11 and passes between light source 16 and photocell 20. Fluctuations in the transmissivity or scattering of the fluid passing through section 10a of line 10 are indicated on meter 48 if they occur within a prescribed time period following injection. A source of chemicals 12 and an injector mechanism 14 are located upstream of section 10a to inject a slug of indicator into line 10. If the tested for condition is present in line 10, the addition of indicator will change the transmissivity or scattering of the fluid in section 10a after a short delay and hence the output of photocell 20 will be changed. An injection sensor 30 senses the injection of a slug of indicator into line 10 by injector mechanism 14 and gives a signal to delay circuits 32 and 34. The delay circuit 32 after a first delay sufficient for the injected chemical to have reached line section 10a activates sampling circuit 36 which is connected to photocell 20 and transmits a signal indicative of the transmissivity or scattering of the fluid to holding circuit 38. The signal can represent the value of the transmissivity or scattering averaged over a short time period, the integral of the value over such a period, or any other suitable form. The delay circuit 34 after a second delay sufficient for the injected chemical to have been purged from line section 10a activates sampling circuit 42 which is connected to photocell 20 and transmits a signal indicative of the transmissivity or scattering of the fluid to holding circuit 44. The holding circuits 38 and 44 thereafter transmit their signals to the subtracting circuit 46 which compares the two signals and indicates any difference therebetween on meter 48.

In each of the above descriptions of the operation of the embodiments of the invention, a single cycle has been described and it is obvious that this cycle will be repeated. The frequency and regularity of the periods of addition of indicator will be a function of the injector mechanism chosen. Likewise, it will be apparent to those skilled in the art that a control function and/or a sampling function can be had in addition to or in substitution for the indicating function.

In summary, this invention provides a method and apparatus for testing for the presence of a chemical, such as a heavy metal, or a condition, such as pH, where a precipitate or color change may be produced upon the introduction of a chemical, even in the presence of a masking contaminant, since the masking effect of the contaminant is reduced by determining fluctuations of, or the differences in, the transmissivity or scattering of light passing through the fluid rather than the value of the transmissivity or scattering after the addition of the indicator.

This invention is applicable to standard tests other than those specifically described above such as may be found in any reference on colorimetric analysis such as Bruno Lange, "Kolorimetrische Analyse," Berlin 1944.

Although preferred embodiments of the present invention have been illustrated and described, other changes will occur to those skilled in the art. It is therefore intended that the scope of the present invention is to be limited only by the scope of the appended claims.

I claim:
1. A method for eliminating the effects of optical system deterioration and the presence of interfering contaminants when determining the presence of a condition in a flowing fluid and including the steps of:
flowing the fluid to be tested through the light path of an optical testing means;
using said optical testing means to periodically determine an optical characteristic of the flowing fluid and producing a signal indicative of said optical characteristic;
storing said signal indicative of said optical characteristic of the fluid;
periodically introducing a predetermined amount of an indicator indicative of the presence of the tested-for condition into the fluid to be tested at a point upstream of said optical testing means to cause a chemical reaction and to change said optical characteristic of the fluid to be tested only in the presence of the tested-for condition;
flowing the fluid to which the indicator has been added through the identical light path of said optical testing means as said fluid to be tested;
using said optical testing means for synchronously determining said optical characteristic of the flowing fluid to which indicator has been added and producing a signal indicative of said optical characteristic;
storing said signal indicative of said optical characteristic of the fluid to which said indicator has been added; and comparing said stored signals indicative of said optical characteristic whereby the optical effects produced by the presence of interfering contaminants in the fluid, by nonsynchronous changes in the fluid and by the deterioration of said optical testing means will cancel out and the presence of the tested-for condition will be indicated by a difference in said optical characteristic determined periodically.

2. A cyclic colorimetry system for eliminating the effects of optical system deterioration and the presence of interfering contaminants when determining and indicating the presence of a condition in a flowing fluid to be tested and comprising;

light source means;

photocell means for producing an output signal proportional to the amount of light from said light source means which is incident thereon;

means for causing the fluid to flow intermediate said light source means and said photocell means and including a transparent portion defining a light path between said light source means and said photocell means;

indicator means for producing a chemical reaction in the fluid in the presence of the tested-for condition and to thereby produce a change in an optical characteristic of the fluid only in the presence of the tested-for condition;

means for periodically causing the introduction of a predetermined quantity of said indicator means into the fluid at a point upstream of said light source means and said photocell means;

means for sensing the introduction of said indicator means into the fluid and for producing a synchronizing actuating signal;

first means responsive to said actuating signal for determining the output signal of said photocell means after a first predetermined time period and for producing a first signal output representative of the tested-for optical characteristic of the fluid to which said indicator means has been added;

second means responsive to said actuating signal for determining the output signal of said photocell means after a second predetermined time period which is longer than said first predetermined time period to permit the purging of fluid to which said indicator means has been added to produce a second signal output representative of the tested-for optical characteristic of the untreated fluid;

means for storing said first and second signal outputs; and means for comparing said stored first and second signal outputs whereby optical effects produced by the presence of interfering contaminants, by nonsynchronous changes in the fluid and by deterioration of the optical system comprising the light source means, the photocell means and said light path are canceled and the presence of the tested-for condition is indicated by any difference in said stored first and second signal outputs.

* * * * *